United States Patent [19]

Doyle et al.

[11] 4,298,689
[45] Nov. 3, 1981

[54] GONORRHEA DIAGNOSTIC TEST

[75] Inventors: Ronald J. Doyle, Jefferson Town; Kenneth F. Keller, Anchorage; Robert L. Schaefer, Louisville, all of Ky.

[73] Assignee: Research Corporation, New York, N.Y.

[21] Appl. No.: 945,211

[22] Filed: Sep. 25, 1978

[51] Int. Cl.² ............................................. C12Q 1/04
[52] U.S. Cl. .................................. 435/34; 23/230 B; 424/12
[58] Field of Search ................ 195/103.5 M, 103.5 R, 195/103.5 A; 23/230 B; 424/7, 12, 13; 435/34, 871, 29

[56] References Cited

U.S. PATENT DOCUMENTS

| 4,029,756 | 6/1977 | Gaafar | 195/103.5 A X |
| 4,108,729 | 8/1978 | Mennen | 195/103.5 M X |
| 4,126,416 | 11/1978 | Sears | 23/230 B |
| 4,140,581 | 2/1979 | Weetall | 195/103.5 M X |

Primary Examiner—Robert J. Warden
Attorney, Agent, or Firm—Wyatt, Gerber, Shoup, Scobey & Badie

[57] ABSTRACT

Method of diagnosing *Neisseria gonorrhoeae* infections utilizing plant lectins which have an affinity for N-acetylglucosamine.

18 Claims, No Drawings

GONORRHEA DIAGNOSTIC TEST

BACKGROUND OF THE INVENTION

Current methods for definitively diagnosing *Neisseria gonorrhoeae* (N.g.) infections are time consuming and expensive. The sugar fermentation test, which is most often used in clinical laboratories, requires an incubation period of 6 to 48 hours after primary isolation. Other tests which have been suggested to increase the speed of testing generally require that the testing laboratory have relatively expensive instrumentation available such as fluorescence microscopes or radioimmunoassay equipment. There is a genuine need for a facile, accurate, reproducible, sensitive, specific, inexpensive test for screening large numbers of people. It has been previously demonstrated that lectins extracted from a variety of plants can be used to selectively agglutinate specific types of red blood cells, bacteria and yeasts. A clinical application of this phenomenon has been utilized in identifying specific red blood cell types. Ottensooser et al. have shown that a lectin isolated from *Wisteria floribunda* seeds would agglutinate certain Group C streptococcus, but would not affect other serotypes of streptococci, see (*Infection and Immunity*, Vol. 9, No. 5, 971-973 (1974). These workers even suggested that the laboratory tests might be extended to clinical applications. However, there have been no reports of any clinical applications to determine the presence of any kind of infections in humans.

THE INVENTION

A test has now been discovered for detecting the presence of N.g. infections in humans which meets all of the criteria set forth above, and is well adapted to large population screening. The test comprises a method for the detection of N.g. infections of humans.

It has been discovered that plant lectins which possess an affinity for N-acetylglucosamine residues will react specifically with N.g. microorganisms since these microorganisms are characterized by the presence of available N-acetylglucosamine on the cell surface. The resulting reaction can be detected by any of a number of available means. Perhaps the most convenient method of detection is the macroscopic-slide agglutination test the accuracy of which may be enhanced by microscopic examination. It is also possible to label or tag the lectin and detect the presence of a reaction product by detecting the tag without effecting agglutination. For example, the lectin can be tagged with a fluorescein dye, that is, a dye which fluoresces when exposed to ultraviolet light such as fluorescein itself, rhodamine and auramine. These are presently preferred, but other labels, for example, isotopic labels such as $^{14}C$, $^{125}I$, $^{131}I$, and $^{35}S$; or enzyme labels such as peroxidase, B-glucuronidase, B-D-glucosidase, B-D-galactosidase, urease, glucose oxidase plus peroxidase, galactose oxidase plus peroxidase and acid phosphatase may also be employed. With these labels the reaction product is not, strictly speaking, an agglutination product such as is observed when the lectin is contacted with the N.g. microorganisms on a cell growth culture. These procedures are effective in testing exudates resulting from human infection.

The presently preferred lectins for use in the test are wheat germ lectin, *Bandeiraea simplicifolia* (B.s.) lectin, and Ulex europeus (U.e.) lectin. All of these are known lectins which can be isolated by known procedures.

Wheat germ lectin is prepared by a modification of the procedure of Bloch et al; *Biochem. Biophys. Res. Comm.* 58(1):13 (1974). In the process, crude extract from wheat germ is dissolved in 0.05 M Tris HCl (pH 8.5) and poured over a chitin column. Non-bound proteins are eluted from the column with 0.01 M Tris HCl (pH 8.5) containing 1 M NaCl, until the eluate shows an absorbance of less than 0.04 at 280 nm. The bound wheat germ lectin is then eluted from the column with 0.05 N HCl until the eluate shows an absorbance of less than 0.04 at 280 nm. Fractions are pooled and precipitated with 50% $(NH_4)_2SO_4$. They are then dialyzed overnight against $PO_4$ buffered saline (pH 7.2) (0.05 M $PO_4$, 0.15 M NaCl) to remove the ammonium sulfate and provide a phosphate buffered saline (PBS) solution of the lectin.

For the preparation of B.s. lectin, the seeds of B.s. (25 gm) are ground in a Waring blender, and the pulverized material "de-fatted" by stirring overnight with 400 ml of hexane. After air drying, the lipid-free pulp is stirred with PBS (pH 7.2) overnight to extract the lectins. The protein lectins are precipitated with 60% $(NH_4)_2SO_4$ and dialyzed overnight against PBS (pH 7.3). Final purification of the lectin may be achieved by the use of the chitin column as described above; see Iyer et al. *Arch. of Biochem. and Biophys.* 177, 730 (1976).

The *Ulex europeus* lectin may be prepared according to the method of Matsumoto and Osawa; *Archives of Biochem. and Biophys.* 140, 484 (1970). According to the method, a finely ground quantity of *Ulex europeus* seeds is extracted with 0.9% sodium chloride solution. The extract is brought to 70% saturation with ammonium sulfate, and the resulting precipitate is dialyzed against distilled water and freezedried. Further purification of the N-acetylglucosamine binding lectin can then be achieved by DEAE-cellulose chromatography or by affinity chromatography on a chitin column as described above.

The methods of this invention are capable of detecting the presence of N.g. cells in a variety of media by a simple slide agglutination test. As suggested above, the tagged lectin can be used to detect directly the presence of N.g. microorganisms in exudates resulting from human infection.

In one embodiment of the invention, the test with humans suspected of haboring an N.g. infection is carried out as follows:

1. A specimen, normally a genital or anal specimen is obtained from the suspect.
2. The specimen is cultivated in a conventional manner on a Thayer-Martin Medium. Growth in this medium suggests that there may be a Neisseria microorganism present.
3. A sample of the growth culture is stained to determine if it is a gram negative diplococcus.
4. A sample of the growth culture is subjected to the oxidase test.
5. If the colonies growing on the Thayer-Martin medium are gram negative diplococci and oxidase positive, they are suspended in an aqueous buffer medium at a pH of from 4 to 10. The optimum density of the suspension is that of a standard No. 3 McFarland tube.
6. The suspension is then contacted with a plant lectin known to react specifically with N-acetylglucosamine. If there is an agglutination reaction, the test is considered positive for the presence of N.g. microorganisms, providing that the negative control (culture plus buffer only) shows no agglutination reaction.

The preferred procedure for detecting agglutination is to view a sample of the treated suspension macroscopically. As indicated above, the presence of N.g. can also be detected instrumentally utilizing lectins which are tagged with enzymatic, isotopic or fluorescent labels.

The usual buffer employed to maintain the desired pH is PBS, although other buffers such as imidazole, Tris HCl, or ethanolamine hydrochloride may be employed.

The presently preferred testing procedure is an agglutination test performed as follows:

1. A Gram stain and oxidase test is performed on suspect colonies growing on Thayer-Martin medium. If the Gram stain reveals Gram negative diplococci and the oxidase test is positive proceed with the agglutination test.
2. Pick up several colonies with a cotton swab and emulsify in approximately 1.0 ml PBS (pH 7.2). Turbidity of the suspension should approximate a No. 3 McFarland opacity standard.
3. Add one drop of bacterial suspension to each of two wells in a slide (Boerner plate). To the first well, add 1 drop of purified wheat germ lectin (protein conc. in PBS 0.1–1.0 mg/ml and to the other well add 1 drop PBS.
4. Place slide on a rotary shaker for approximately 5 minutes.
5. Read test visually. An agglutination in well number one constitutes a positive test for *Neisseria gonorrhoeae*. If autoagglutination occurs in well number two (the PBS control) the test is not valid.

The concentration of lectin in the buffer solution is, typically, from 0.1 to 1.0 mg/ml since this is the concentration range at which it is usually isolated. Appreciable variation from this range can be tolerated, however, without adverse effects. The test is sensitive at a concentration as low as 0.1 mg/ml. A concentration as high as 2 mg/ml can be employed, but with no particular advantage over the lower concentration.

The temperature at which the test is conducted is not critical. Normally, ambient temperature, i.e., from 20° C. to 40° C. is suitable. The time for agglutination to take place is typically, from 5 to 8 minutes.

The above test exemplifies the use of wheat lectin. The procedure is substantially similar with other N-acetylglucosamine binding lectins. The control is a normal precaution which is recommended for all tests of this nature. The use of a combination of two lectins greatly increases the confidence level of the test. It has been observed that the wheat germ lectin is slightly more sensitive as an agglutination agent than the B.s. lectin, although the latter is slightly more specific. Both, however, are capable of extremely high orders of sensitivity and specificity. In tests on a series of specimens from a variety of sources, wheat germ lectin was found to agglutinate 99% of 155 confirmed strains of N.g. positives. In tests employing 16 strains of *Neisseria meningitides* (N.m.) strains, wheat germ lectin gave only one false positive. The foregoing false positive was a serogroup X which is rarely, or ever, found in the urogenital tract.

The test methods described and claimed herein have been compared for efficacy with the widely employed fluorescein tagged antibody test (FTA). In the comparison, six gonococcal cultures which were reported as giving negative results in the FTA test despite the fact that they had separately been determined to be N.g. cultures by other methods were tested with wheat germ lectin in accordance with the procedures described above. Five of the six cultures gave a positive agglutination reaction.

Wheat germ lectin can be tagged for use in this invention by the procedure of Cronin et al; Cytobios. 2, 225 (1970). In the procedure, a solution of 0.2 ml of wheat germ lectin (titer for guinea pig red cells 1 to 64) in carbonate buffered saline pH 9.5 is dialyzed overnight at 4° C. against 20 ml of a 0.01% solution of fluorescein isothiocyanate in 0.05 molar carbonate buffer in saline. The content of the dialysis tube is applied to a Sephadex G-25 column (1.5 by 43 cm) and eluted with PBS in 1.0 ml fractions collected at the rate of 1 ml per minute. The fractions are tested against guinea pig red cells for agglutination and staining ability. Active fractions pooled and stored at 4° C. are stable for 2 months.

A suitable oxidase test for use in this invention is carried out as follows:

Several drops of p-aminodimethylaniline oxalate 1% solution is placed on a piece of filter paper. A portion of the bacterial colony is rubbed on the paper with a wire loop. Development of a purple color within 10 to 15 seconds is indicative of a positive oxidase test.

What is claimed is:

1. A method for detecting the presence of *Neisseria gonorrhoeae* microorganisms which comprises contacting, at a pH of from 4 to 10, a sample suspected of containing a *Neisseria gonorrhoeae* microorganism with a plant lectin, the said lectin being characterized as one which reacts specifically with N-acetylglucosamine and testing resulting mixture for the presence of a reaction product formed by reaction between the lectin and N-acetylglucosamine on the cell surface of said *Neisseria gonorrhoeae* microorganism, wherein the presence of such reaction product is a presumptive indication of the presence of a *Neisseria gonorrhoeae* microorganism.

2. A method as in claim 1 wherein the sample is an exudate from a human suspected of an infection of *Neisseria gonorrhoeae* microorganisms.

3. A method as in claim 1 wherein the lectin is tagged with a detectable label selected from the group consisting of fluorescein dye labels, isotape labels and enzyme labels.

4. A method as in claim 3 wherein the lectin is wheat germ lectin tagged with a fluorescein dye.

5. A method as in claim 3 wherein the lectin is one obtained from *Bandeiraea simplicifolia* and that is tagged with a fluorescein dye.

6. A method as in claim 3 wherein the lectin is one obtained from *Ulex europeus* and that is tagged with a fluorescein dye.

7. A method for detecting the presence of *Neisseria gonorrhoeae* microorganisms in a gram negative, oxidase positive culture medium which comprises contacting a suspension of microorganisms from a gram negative, oxidase positive culture medium in an aqueous media at a pH of from 4 to 10 with a plant lectin, the said lectin being characterized as one which reacts specifically with N-acetylglucosamine to effect agglutination caused by reaction between the lectin and N-acetylglucosamine on the cell surface of a *Neisseria gonorrhoeae* microorganism, and detecting the presence of such agglutination, wherein the presence of such agglutination is a presumptive indication of the presence of a *Neisseria gonorrhoeae* microorganism.

8. A method as in claim 7 wherein the culture is generated from a specimen obtained from a human suspected of an infection by *Neisseria gonorrhoeae* microorganisms.

9. A method as in claim 8 wherein the lectin is wheat germ lectin.

10. A method as in claim 8 wherein the lectin is obtained from *Ulex europeus*.

11. A method as in claim 8 wherein the lectin is obtained from *Bandeiraea simplicifolia*.

12. A method as in claim 8 wherein the agglutination is detected macroscopically.

13. A method as in claim 12 wherein the lectin is obtained from *Bandeiraea simplicifolia*.

14. A method as in claim 12 wherein the lectin is wheat germ lectin.

15. A method as in claim 12 wherein the lectin is obtained from *Ulex europeus*.

16. A method as in claim 7 wherein the lectin is wheat germ lectin.

17. A method as in claim 7 wherein the lectin is obtained from *Bandeiraea simplicifolia*.

18. A method as in claim 7 wherein the lectin is obtained from *Ulex europeus*.

* * * * *